United States Patent
Subramanyam (10) Patent No.: US 8,008,930 B2
(45) Date of Patent: Aug. 30, 2011

(54) CHARACTERIZATION TECHNIQUE FOR DIELECTRIC PROPERTIES OF POLYMERS

(75) Inventor: Guru Subramanyam, Dayton, OH (US)

(73) Assignee: University of Dayton, Dayton, OH (US)

( * ) Notice: Subject to any disclaimer, the term of this patent is extended or adjusted under 35 U.S.C. 154(b) by 639 days.

(21) Appl. No.: 11/909,646

(22) PCT Filed: Mar. 23, 2006

(86) PCT No.: PCT/US2006/010829
§ 371 (c)(1), (2), (4) Date: Sep. 25, 2007

(87) PCT Pub. No.: WO2006/104902
PCT Pub. Date: Oct. 5, 2006

(65) Prior Publication Data
US 2010/0066389 A1    Mar. 18, 2010

(51) Int. Cl.
*G01R 27/26* (2006.01)
(52) U.S. Cl. ....... 324/658; 324/663
(58) Field of Classification Search ............. 324/658
See application file for complete search history.

(56) References Cited

U.S. PATENT DOCUMENTS

| | | | |
|---|---|---|---|
| 7,241,394 B2 * | 7/2007 | Dinu et al. | 216/13 |
| 7,254,151 B2 * | 8/2007 | Lieber et al. | 372/44.01 |
| 7,692,270 B2 * | 4/2010 | Subramanyam et al. | 257/601 |
| 7,719,392 B2 * | 5/2010 | Subramanyam et al. | 333/205 |
| 2007/0013466 A1 * | 1/2007 | Hersey et al. | 333/262 |
| 2007/0069264 A1 * | 3/2007 | Subramanyam et al. | 257/295 |
| 2010/0008825 A1 * | 1/2010 | Subramanyam | 422/82.02 |

OTHER PUBLICATIONS

Subramanyam et al., Microwave Characterization of Electro-optic Polymers, Mar. Res. Soc. Symp. Proc., vol. 734, 2002, p. 249-254.*
Subramanyam, U.S. Appl. No. 60/512,131, Oct. 20, 2003.*
Lipscomb, et al., Developments in organic electro-optic devices at Lockheed, SPIE, vol. 1337, p. 23-34.*
Yoshito, Shudo, JP 06075256, PTO Translation, PTO 10-5585, p. 1-19.*
Rolain et al. "Microwave Permittivity Measurement of Polymers By Deposition on a Coplanar Wave Guide", pp. 333-338, May 2004.
Chinese Notification of First Office Action, Application No. 200680014935.9, University of Dayton, "Characterization Technique For Dielectric Properties of Polymers", Nov. 1, 2010.

* cited by examiner

*Primary Examiner* — Thomas Valone
(74) *Attorney, Agent, or Firm* — Dinsmore & Shohl, LLP (57) ABSTRACT

A test structure for polymer characterization over a wide frequency range, temperature range and under an applied DC electric field is disclosed. A high resistivity silicon substrate is topped by an adhesion layer. A polymer thin-film is deposited on a patterned metal1 layer which is deposited on top of the adhesion layer. A top metal2 layer is deposited on the polymer thin-film and patterned to form a CPW transmission line. A single bias voltage is applied to the center conductor of the CPW transmission line on metal2 and influences dielectric properties of the polymer. The dielectric permittivity and the loss-tangent of the polymer can be derived as functions of electric field and temperature by measuring the swept frequency scattering parameters and matching the experimental frequency response to the modeled frequency response. The electrical conductance properties of the polymer can be accurately characterized using the test structure over a wide temperature range.

14 Claims, 9 Drawing Sheets

CHARACTERIZATION TECHNIQUE FOR DIELECTRIC PROPERTIES OF POLYMERS

The present invention relates generally to a test structure for polymer thin film characterization, and in particular, to an effective and efficient test structure for nonlinear optical (NLO) polymer thin film characterization over a wide frequency range and a wide temperature, under an applied electric field.

Polymer thin-films are attractive for optical and photonics applications due to their processability, low optical and microwave loss, and low cost. In addition, the ability to easily measure the dielectric properties of polymers over a wide frequency range is important in the design of microwave photonic devices such as high-speed optical modulators. However, the dielectric characteristics of new polymers may not be known. Additionally, it is beneficial to know the polymers' dielectric characteristics over a wide frequency range, as functions of electric field as well as temperature especially for nonlinear optical polymers used in photonics applications.

Therefore, there is a need for measurement of dielectric properties of polymer based thin-films over a wide frequency range as functions of electric field and temperature.

This invention provides electric field poling in nonlinear optical polymers for photonics applications. In one embodiment, a coplanar waveguide based capacitance test structure with two terminals can be used for the characterization of the electric poling of Deoxyribonucleic Acid (DNA)-based polymers or any other electro-optical (EO) polymers. High resistivity silicon wafer is used as the substrate. An adhesion layer (of chromium or titanium) is applied directly onto the high resistivity silicon wafer. A bottom metal layer (metal1 layer) is deposited on top of the adhesion layer and patterned. A polymer thin film is deposited on top of the patterned bottom metal layer. A top metal electrode (metal2 layer) is deposited on the polymer thin-film layer through a shadow mask and patterned to form a coplanar waveguide (CPW) transmission line. A single bias voltage is applied to the center conductor of the CPW transmission line on metal2 layer and influences the dielectric properties of the polymer thin-film. The dielectric permittivity and the loss-tangent of the polymer thin-film can be derived as functions of electric field and temperature by measuring the swept frequency scattering parameters (S-parameters) and matching the experimental frequency response to a model frequency response. In addition, the electrical conductance measurements (i.e., current vs. voltage) can also be obtained for the polymer as a function of temperature.

Accordingly, the present invention provides a polymer characterization test structure that can determine the dielectric properties, as well as electrical conductance properties, of a polymer thin-film as functions of both electric field and temperature, over a wide frequency range.

Another feature of the embodiments of the present invention is to provide for a capacitive test structure to characterize polymers at microwave frequencies under an applied DC electric field.

Other features of the embodiments of the present invention will be apparent in light of the description of the invention embodied herein.

The following detailed description of specific embodiments of the present invention can be best understood when read in conjunction with the following drawings, where like structure is indicated with like reference numerals and in which.

In the following detailed description of the embodiments, reference is made to the accompanying drawings that form a part hereof, and in which are shown by way of illustration, and not by way of limitation, specific embodiments in which the invention may be practiced. It is to be understood that other embodiments may be utilized and that logical, mechanical and electrical changes may be made without departing from the spirit and scope of the present invention.

Two polymers were examined: a DNA based film, deoxyribonucleic acid-hexadecyltrimethylammonium chloride (DNA-CTMA), and Bovine Serum Albumin (BSA). The DNA-CTMA used in this study was formed by precipitating one million molecular weight marine-based DNA into CTMA. BSA is a common protein extracted from cow's blood. The capacitive test structure was used to characterize each polymer. The characterization took place at room temperature and with and without a 20V DC bias. A commercial amorphous polycarbonate (APC) polymer was also tested for reference in order to compares the bio-polymers with a pure polymer.

Figure 1:
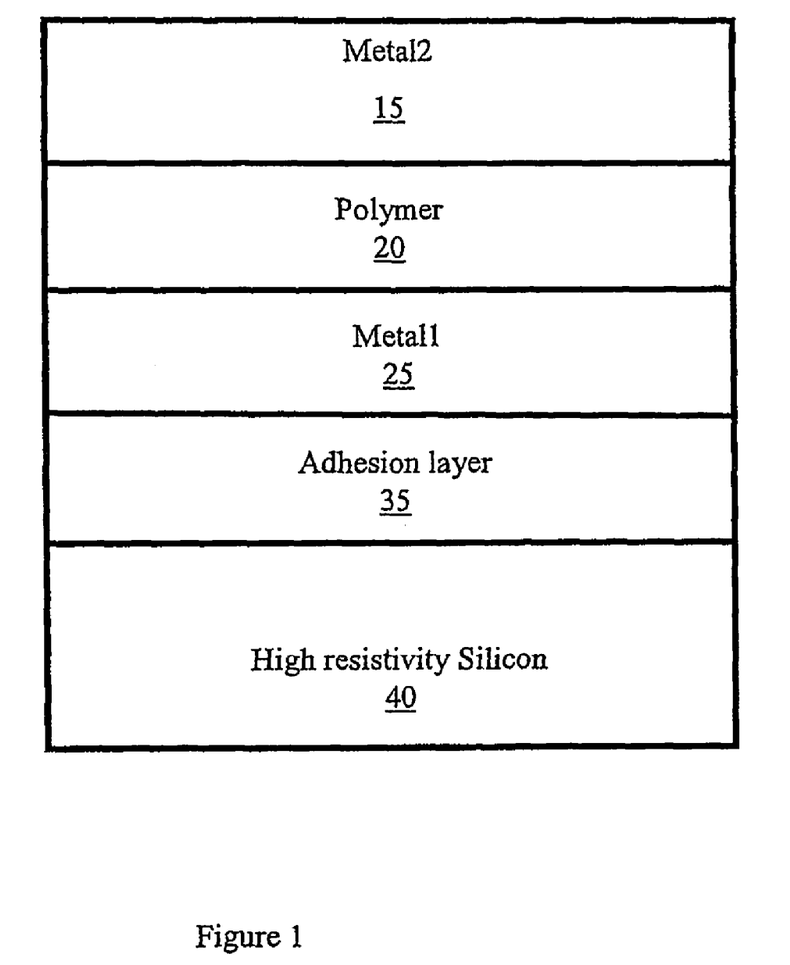
FIG. 1 illustrates a cross-sectional view of multiple layers of a polymer characterization test structure according to one embodiment of the present invention.

FIG. 1 illustrates a cross-sectional view of the multiple layers of a polymer characterization test structure. The polymer characterization test structure is designed on a coplanar waveguide (CPW) transmission line that has a multilayer structure fabricated on a wafer of high resistivity silicon 40. In one embodiment, the high resistivity silicon wafer 40 can be from about 0.01 to about 0.02 inches (or about 0.254 mm to about 0.508 mm) thick. In another embodiment, a layer of silicon dioxide may be present on the high resisitivity silicon wafer 40. As a first step in the fabrication, an adhesion layer 35 is sputtered directly on the high resistivity silicon wafer 40. The adhesion layer 35 can be chromium, titanium or any other suitable material. In one embodiment, the adhesion layer 35 has a thickness of 100 to about 200 Å.

Figure 2A:
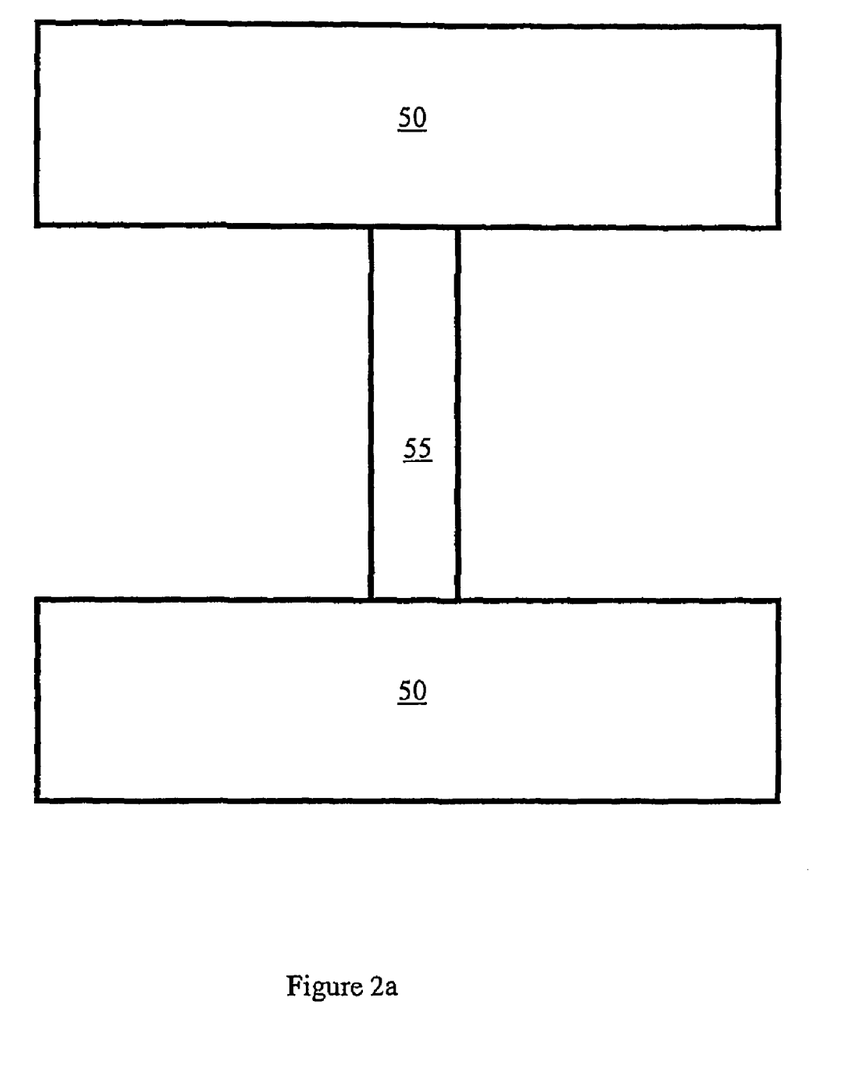
FIG. 2a is a pattern of a bottom metal electrode according to one embodiment of the present invention.

A patterned bottom electrode (metal1 layer) 25 is processed on the adhesion layer 35 by electron-beam (e-beam) deposition (or sputtering) and lift-off photolithography technique. In another embodiment, the patterning of the metal1 layer can be accomplished by performing metal deposition through a shadow mask. FIG. 2a illustrates the pattern of the bottom metallic layer (metal1) 25. The bottom metallic layer (metal1) 25 consists of two ground lines 50 shunted together by a conductor, or shunt line 55. In one embodiment, the conductor can be about 100 µm wide. The bottom metallic layer (metal1) 25 can be platinum, gold or any other suitable metal. In one embodiment, the bottom metallic layer (metal1) 25 is formed from about 7500 to about 10000 Å of gold sputtered onto the adhesion layer 35.

After the lift-off photolithography process, the layer 25 is covered by the polymer thin film 20 that is to be characterized. The polymer thin film 20 is deposited on the bottom metallic layer (metal1) 25 as a thin-film by spin-coating. The polymer thin film 20 can have a thickness of about 100 nm to several microns thick. The polymer thin-film 20 can be any polymer and typically is a nonlinear optical polymer such as, for example, DNA-based polymers or any other NLO/EO polymer. In one embodiment, DNA-CTMA and BSA were examined.

Figure 2B:
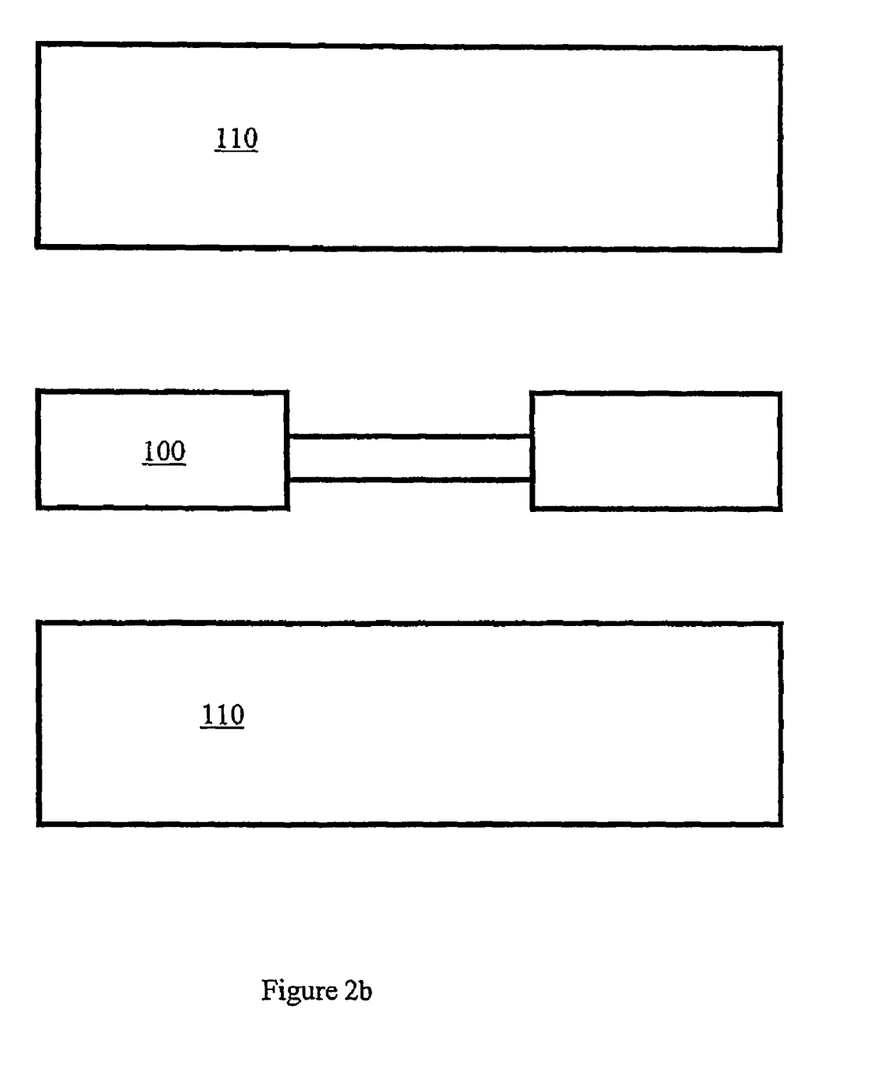
FIG. 2b is a pattern of top metal electrode according to one embodiment of the present invention.

FIG. 2b illustrates the pattern of the top metal electrode (metal2) 15 that is deposited on top of the polymer thin film 20 and patterned to form a CPW transmission line. The top metal electrode (metal2) 15 comprises of the central signal strip 100 and the ground conductors 110 of the CPW transmission line. The top metal electrode (metal2) 15 is prepared by e-beam deposition (or sputtering) through a shadow mask or a lift off photolithography process. This top metal electrode (metal2) 15 may be comprised of gold, platinum, combinations of gold and platinum, or any other suitable metal. In one embodiment, the top metal electrode (metal2) 15 is formed from about 3500 to about 5000 Å of gold deposited on the polymer thin film 20 by e-beam deposition.

Figure 2C:
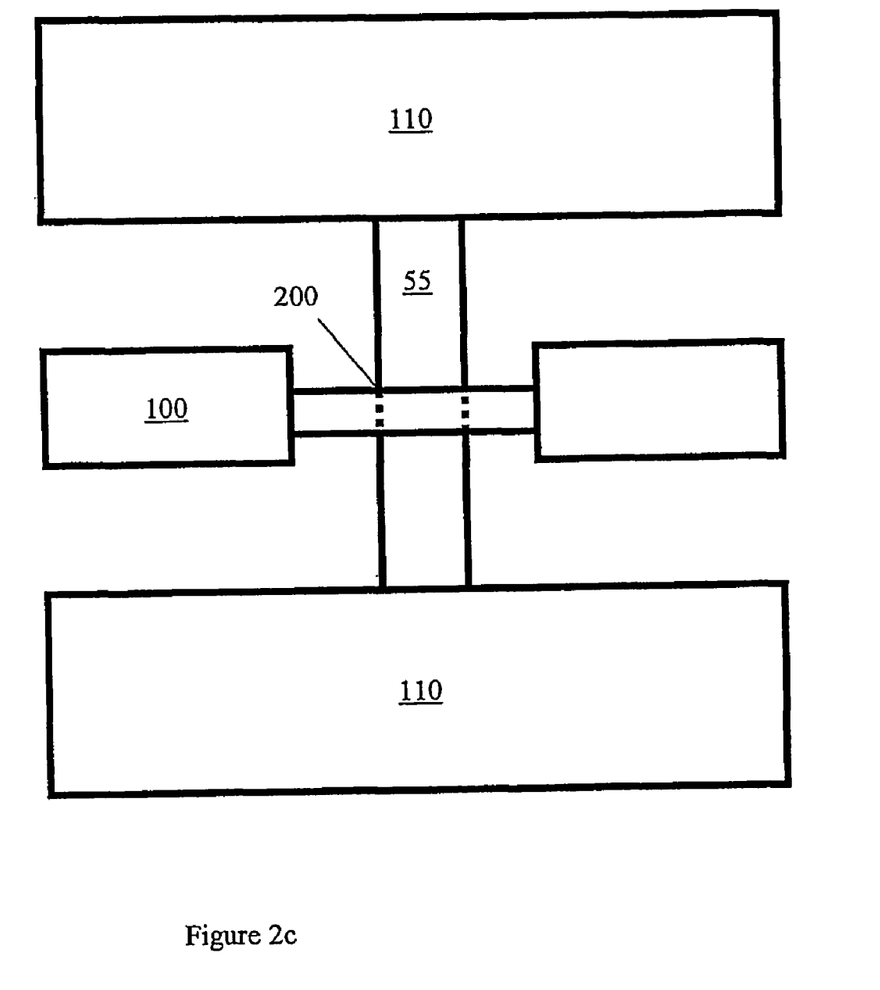
FIG. 2c illustrates a top-view of a polymer characterization test structure indicating the overlapping region of the metal electrodes according to one embodiment of the present invention.

The top view of the finalized CPW is shown in FIG. 2c. In FIG. 2c, the overlap area 200 between the top metal electrode (metal2) 15 and the bottom metallic layer (metal1) 25 is indicated by the dashed lines. The two ground conductors 110 of the top metal electrode (metal2) 15 lie directly above the ground lines 50 of the bottom metallic layer (metal1) 25 and may have the exactly the same dimensions as the ground lines 50 of the bottom metallic layer (metal1) 25. The central signal strip 100 is centered between the ground conductors 110 and is perpendicular to the shunt line 55 of the bottom metallic layer (metal1) 25. In another embodiment, the ground lines 50 of the bottom metallic layer (metal1) 25 may be much larger than the ground conductors 110 of the top metal electrode (metal2) 15 without significantly affecting the functionality of the test structure.

The active region 200 of the test structure capacitance device is defined by the overlap area of the center signal strip 100 of the top metal electrode (metal2) 15 and the shunt line 55 in the bottom metal electrode (metal1) 25. The active region 200 contains the test capacitor. The test structure capacitance device has a large ground pad capacitor that results from the overlap of the ground lines 50 of the bottom metallic layer (metal1) 25 and the ground conductors 110 of the top metal electrode (metal2) 15. The ground line conductors 50 in the bottom metallic layer (metal1) 25 and the ground conductors 110 of the top metal electrode (metal2) 15 are effectively shorted, due to the large capacitance between the two layers. Since the test capacitor is in series with the much larger ground pad capacitor, the effective capacitance is that of the test capacitor. When a DC bias is applied, the DC current passes through the leakage conductance of the test capacitor, the shunt line 55 in the bottom metal electrode (metal1) 25 and the leakage conductance of the ground pad capacitor. This eliminates the need for via holes to ground the bottom metal electrode (metal1) 25. Since the large ground pad capacitor has a higher leakage conductance, the DC bias applied to the signal conductor drops almost entirely across the test capacitor. The DC voltage drives a small DC current through the test capacitor (because of the leakage conductance of the polymer thin-film).

Figure 2D:
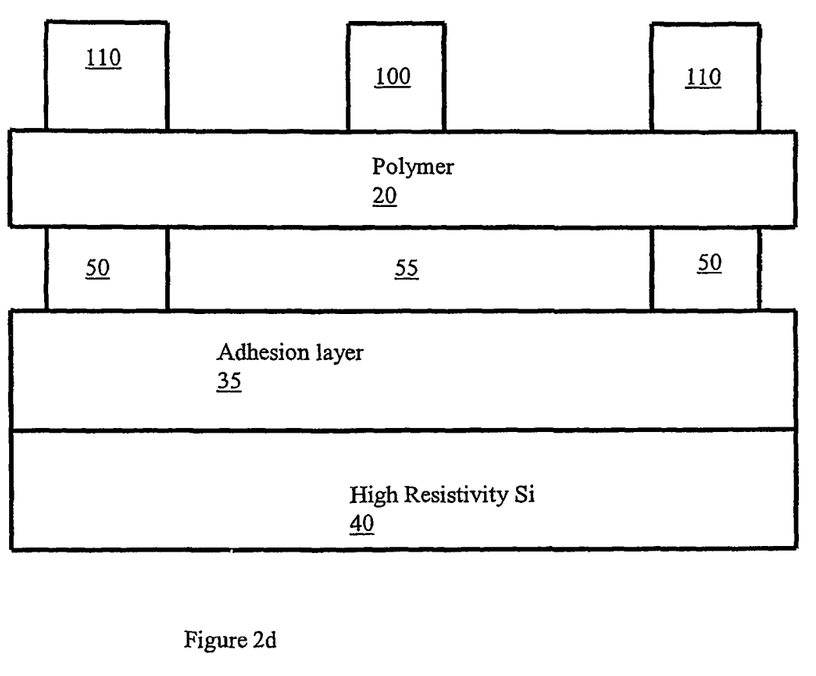
FIG. 2d illustrates a front view of a polymer characterization test structure according to another embodiment of the present invention.

In the cross section of the polymer characterization test structure, as illustrated in FIG. 2d, it is clear that the test structure capacitor is in series with the larger capacitance as defined by the ground electrodes 50 in the bottom metallic layer (metal1) 25 and the ground conductors 110 in the top metal electrode (metal2) 15, resulting in the effective capacitance of the test structure capacitor. The NLO polymer is subjected to a DC electric field by applying a DC voltage between the central signal strip 100 of the CPW (using CPW probes, for example) and the ground conductors 110. The DC electric field, or temperature, may change the relative permittivity of polymer thin-film, and hence the capacitance of the test structure. The DC field or temperature may also affect the loss-tangent of a single layer polymer film or multilayered polymer film.

In one embodiment, the width of the center signal strip 100 of the CPW and the spacing between the center signal strip 100 and ground conductors 110 were chosen so that the characteristic impedance is close to about 50Ω and the line losses are minimized. The CPW line has the dimensions of Ground-Signal-Ground being 300 µm/100 µm/300 µm for DC-20 GHz on the high resistivity silicon substrate 35. The spacing (S) between the center signal strip 100 and ground conductors 110 is taken as 100 µm and the geometric ratio of the CPW line (k=W/(W+2S)) is equal to 0.333. The device area is approximately 1000 µm by 500 µm. The area of the overlap of the top metal electrode (metal2) 15 and the bottom metallic layer (metal1) 25 can be from 25 µm² to 1000 µm².

In one embodiment, a network analyzer and an on-wafer microwave probe station were used to measure the scattering parameters (S parameters) of the capacitive test structure. The setup used to measure the S parameters was a two-port network, with one port at each end of the signal line 100 of the top metal electrode (metal2) 15. A two-port network yields a 2×2 matrix of S parameters that relate the reflected waves (or voltages) to the incident waves (or voltages). The procedure for the experimental determination of S parameters used the following steps. First, the network analyzer and probe station were calibrated to the device over the frequency range of interest (1-20 GHz) using a Line-Reflect-Reflect-Match (LRRM) calibration as known in the art. Then, the DC bias voltage was applied to the signal lead of the probe (when applicable). Finally, the S parameters were recorded and saved. These S parameters helped determine the exact values in the electrical model. The measurements can be extended to higher frequencies up to about 100 GHz. In addition, measurements can be performed at various sample temperatures using a thermal chuck.

Figure 3:
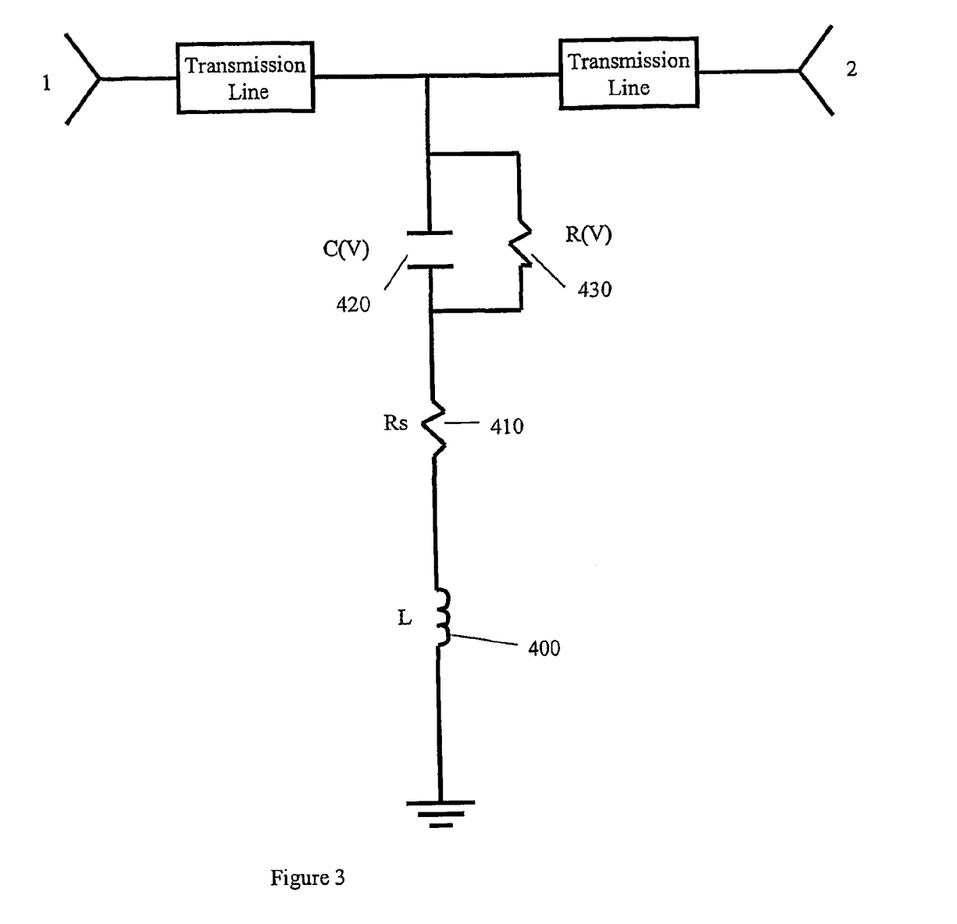
FIG. 3 represents the electric circuit model of the polymer characterization test structure of FIG. 2d according to one embodiment of the present invention.

The measured S parameters were then imported into the Applied Wave Research, Inc. (AWR) Microwave Office simulation package or a Microsoft Excel worksheet. Using the electrical model for the test structure, as shown in FIG. 3 fig:electrical model, the electrical parameters were determined. First, an initial estimate of the values for the electrical model of the capacitive test structure was made. Then, the electrical model was optimized to match the experimental results across the frequency range. This procedure was repeated for each capacitive test structure at every bias voltage and every temperature yielding the specific values for the electrical model.

FIG. 3 represents a simple equivalent electric circuit model of the polymer thin film characterization test structure illustrated in FIG. 2d. The test capacitance of the polymer in the active region is represented by C(V) 420. The shunt resistance modeling the leakage conductance of the test capacitor is represented by R(V) 430. The parasitic inductance and resistance for the test capacitor are represented by L 400 and Rs 410, respectively. The specific values were determined by fitting the circuit model to the experimental results, as described above. The electrical model and the measured S parameters were used to calculate the dielectric constant and the loss tangent of the polymer thin film 20.

The electrical circuit model is obtained by shunting the capacitor. The shunt resistance R 430 of the capacitor characterizes the conductance through the polymer thin-film 20 which is determined by the loss-tangent of the polymer thin film 20 and is also a function of electric field and temperature. The capacitance C(V) 420 can be obtained by the standard parallel plate capacitance calculation, with the dielectric permittivity of the polymer thin-film 20 being characterized, and the overlap area 200 of the center signal strip 100 and the shunt line 55. The dielectric constant of the polymer thin film 20 is a function of both the electric field and temperature. The device capacitance C(V) 420 is given by:

$$C(V) = \epsilon_0 \cdot \epsilon_r \cdot A/t_p \quad (1)$$

where $\epsilon_0$ is the dielectric permittivity of free space, $\epsilon_r$ is the dielectric permittivity of the polymer thin film 20 being characterized, A is the area of overlap 200 of the top center signal strip 100 and the shunt conductor 55 within the capacitive test structure, and $t_p$ is the thickness of the polymer thin film 20.

Equation 1 can be re-written to directly calculate the dielectric constant, $\epsilon_r$, from the capacitance from the parallel plate capacitor consisting of the polymer thin film 20 in the active region as Equation 2:

$$\epsilon_r = C(V) t_p / \epsilon_0 A \quad (2)$$

The series resistance (Rs) 410 of the shunt conductor line in the bottom metal layer (metal1) 25, where the signal is shunted to ground is calculated using Equation 3:

$$R = l/(\sigma w t) \quad (3)$$

where, σ is the conductivity of metal used in the top metal electrode (metal2) 25, w is the width of the conductor, l is the length of the line shunting to ground, and t is the thickness of the conductor.

The inductance 400 (L) of the line is calculated using Equation 4:

$$L = (Z_0/(2\pi f)) \sin(2\pi l/\lambda_g) \quad (4)$$

where, $Z_o$ is the characteristic impedance of the CPW transmission line, f is the operating frequency, and $\lambda_g$ is the guide-wavelength.

The shunt resistance 430 (R(V)) of the test structure can be calculated using Equation 5:

$$R(V) = 1/(\omega C(V) \tan \delta) \quad (5)$$

where, C(V) 420 is the capacitance shown in FIG. 3 at a single bias voltage, w is the angular frequency and tan δ is the loss-tangent of the polymer thin film 20 being characterized.

Equation 5 can be re-written to directly calculate the loss tangent, tan δ, from the electrical model of the capacitive test structure as Equation 6:

$$\tan \delta = 1/\omega R(V) C(V) \quad (6)$$

By matching the experimental frequency response to the modeled frequency response, the effect of electric poling can accurately be characterized as a function of both electric field and the temperature.

The procedure outlined above yielded S21 (in Decibels, dB), the ratio of the transmitted power to the input power, as a function of frequency for each sample. Examples of the S21 values for two test structures are plotted in FIG. 6. One test structure had a 2.1 μm thick layer of BSA polymer film, and the other had a 1.7 μm thick layer of Low-density DNA-CTMA (LDNA). For comparison, the frequency response for a test structure with a pure APC polymer layer is also shown. From the data obtained, the loss tangents and dielectric constants were computed. The means and standard deviations of the microwave parameters, for the measured capacitive test structures on an individual wafer, were calculated at each set of conditions. The results from one sample of DNA-CTMA, one of BSA and one of APC are summarized in Table 1. Table 1 illustrates the microwave dielectric properties calculated from one example wafer of DNA-CTMA and one of BSA, with dielectric properties listed as mean-square standard deviation, for a set of three samples.

TABLE 1

| Polymer and bias | $\epsilon_r$ | tanδ (20 GHz) |
|---|---|---|
| DNA-CTMA - 0 V | 6.639 ± 0.355 | 0.189 ± 0.024 |
| DNA-CTMA - 20 V | 6.639 ± 0.355 | 0.200 ± 0.017 |
| BSA - 0 V | 7.019 ± 0.531 | 0.234 ± 0.021 |
| BSA - 20 V | 6.234 ± 0.488 | 0.274 ± 0.042 |
| APC | 5.18 ± 0.03 | 0.18 ± 0.02 |

Figure 6:
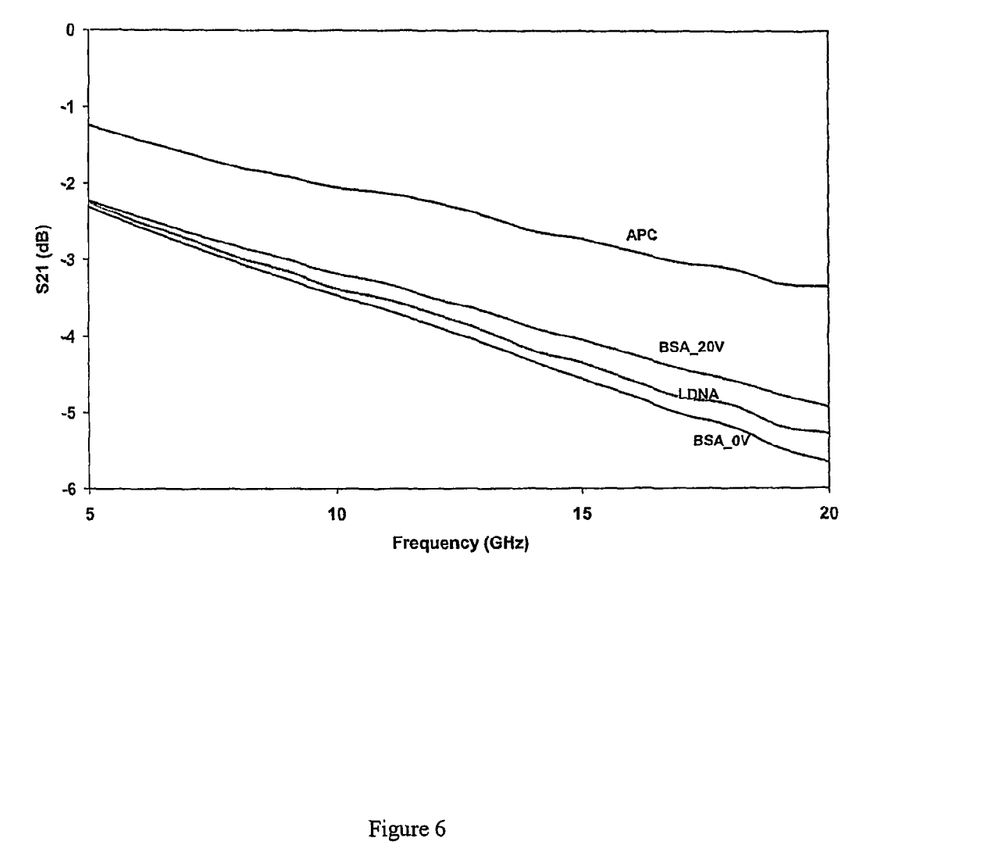
FIG. 6 illustrates the frequency response for the three test structures according to another embodiment of the present invention.

FIG. 6 also illustrates the measured bias dependence of frequency response of S21 for the low density DNA-CTMA and BSA films for zero-bias and 20 V applied at room temperature. The response shows that the dielectric properties of the BSA polymer thin film were tunable with the applied DC bias. This result indicates that the dielectric constant and the loss-tangent were dependent upon voltage at room temperature. DNA-CTMA, however, did not exhibit the dielectric tunability at room temperature. The frequency response for an unbiased APC polymer is also shown in FIG. 6 as point of reference.

Therefore, a new capacitive test structure was developed for characterization of polymer thin films over a wide frequency range and temperature range under an applied electric field. The effect of applying an electric field to the polymer thin film was determined through the use of this new capacitive test structure device. The experimental results show that the dielectric properties of polymer thin films can be accurately characterized over a broad frequency range. The test structure is also useful to obtain the electrical conductance properties of polymer thin-films by measuring the leakage current for each bias voltage, as a function of temperature.

Figure 4:
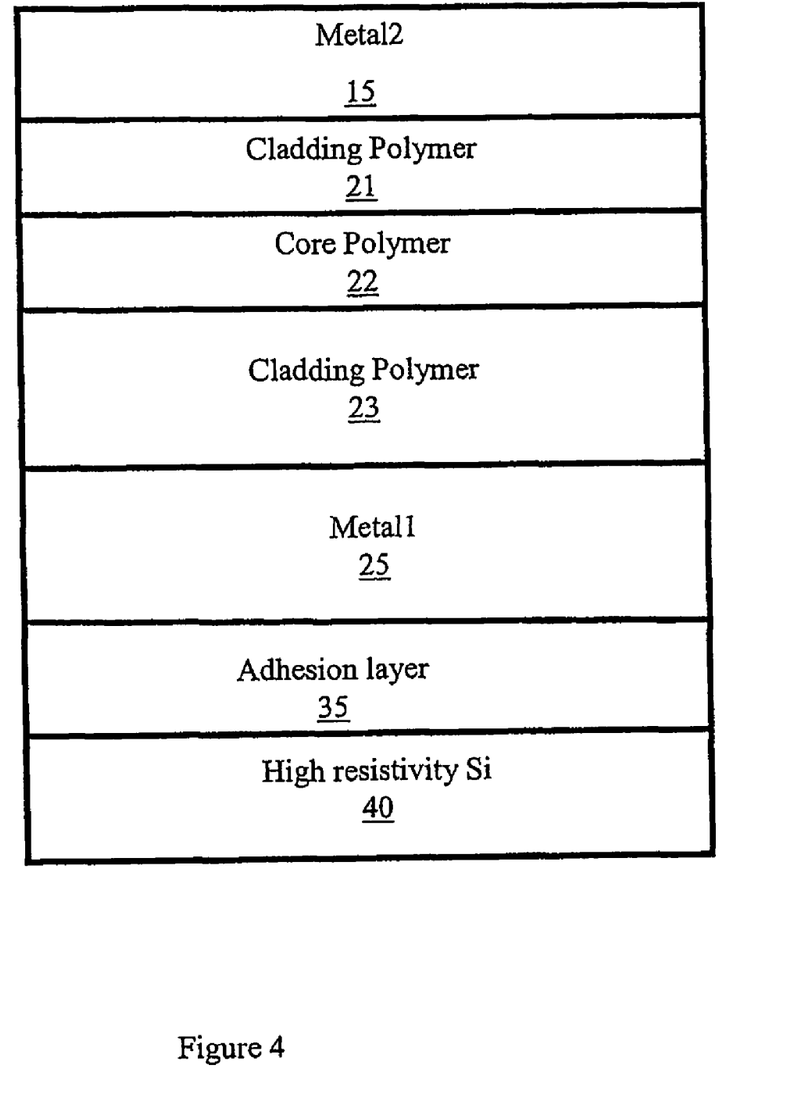
FIG. 4 illustrates a cross-sectional view of the multiple layers of triple stack (clad/core/clad) of polymers of the polymer characterization test structure according to another embodiment of the present invention.
Figure 5:
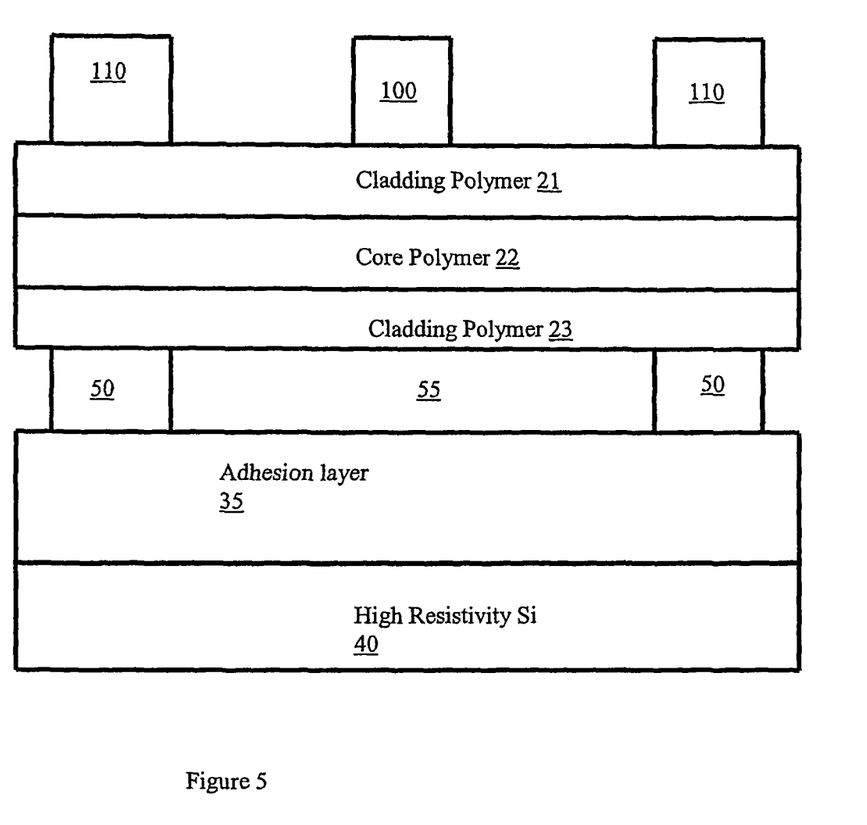
FIG. 5 illustrates a front view of the multiple layers of triple stack (clad/core/clad) of polymers of the polymer characterization test structure according to another embodiment of the present invention.

Other test structures are possible, such as coplanar transmission lines, that can be used for characterizing the in-plane poling characteristics of the polymer thin films. For example, the parallel plate capacitance test structure can also be used for studying the electric poling on multiple polymer thin-film layer stacks. Such multiple polymer thin-film layer stacks are illustrated in FIGS. 4 and 5. The applicable electrical model of a triple stack (clad/core/clad) of polymers may also be obtained.

It is noted that terms like "preferably," "commonly," and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

The invention claimed is:

1. A capacitive test structure for determining dielectric properties of a polymer thin film, the structure comprising:
    a substrate;
    an adhesion layer applied to said substrate, said adhesion layer having a thickness of from about 100 Å to about 200 Å;
    a patterned bottom metal layer deposited on said adhesion layer, wherein said polymer thin film is deposited on said patterned bottom metal layer, said patterned bottom metal layer comprising:
        at least two ground lines; and
        a shunt conductor shunting together said at least two ground lines; and
    a top metal electrode deposited on said polymer thin film, wherein said top metal electrode is patterned to form a coplanar waveguide transmission line.

2. The capacitive test structure of claim 1, wherein said dielectric properties of said polymer thin film comprise dielectric permittivity, loss tangent and combinations thereof.

3. The capacitive test structure of claim 1, wherein said polymer thin film comprises a nonlinear optical polymer.

4. The capacitive test structure of claim 1, wherein said substrate comprises of high resisitivity silicon.

5. The capacitive test structure of claim 1, wherein said substrate has a thickness of from about 0.01 inches to about 0.02 inches.

6. The capacitive test structure of claim 1, wherein said adhesion layer comprises chromium, titanium or combinations thereof.

7. The capacitive test structure of claim 1, wherein said patterned bottom metal layer comprises platinum, gold or combinations thereof.

8. The capacitive test structure of claim 1, wherein said patterned bottom metal layer has a thickness of from about 7500 Å to about 10000 Å.

9. The capacitive test structure of claim 1, wherein said top metal electrode comprises gold, platinum or combinations thereof.

10. The capacitive test structure of claim 1, wherein said top metal electrode has a thickness of from about 3500 Å to about 5000 Å.

11. The capacitive test structure of claim 1, wherein said top metal electrode comprises:
    at least two ground conductors; and
    a center signal strip, wherein said center signal strip is centered between said at least two ground lines.

12. The capacitive test structure of claim 1, wherein said top metal electrode comprises:
    at least two ground conductors, wherein said at least two ground conductors lie directly above said at least two ground lines of said patterned bottom metal layer; and
    a center signal strip, wherein said center signal strip is centered between said at least two ground conductors and is perpendicular to said shunt conductor of said patterned bottom metal layer.

13. The capacitive test structure of claim 12, wherein a test capacitor is defined by the overlap area of said center signal strip of said top metal electrode and said shunt conductor of said pattern bottom metal layer.

14. The capacitive test structure of claim 12, wherein the overlap area of said at least two ground conductors of said top metal electrode and said at least two ground lines of said pattern bottom metal layer results in a large ground pad capacitor.

\* \* \* \* \*